United States Patent [19]

Schermerhorn

[11] Patent Number: 5,605,532
[45] Date of Patent: Feb. 25, 1997

[54] FOG-FREE ENDOSCOPE

[75] Inventor: Richard Schermerhorn, Natick, Mass.

[73] Assignee: Vista Medical Technologies, Inc., Carlsbad, Calif.

[21] Appl. No.: 546,271

[22] Filed: Oct. 20, 1995

[51] Int. Cl.$^6$ ........................................................ A61B 1/06
[52] U.S. Cl. .......................... 600/169; 600/176; 600/177
[58] Field of Search ........................... 600/101, 103, 600/118, 160, 169, 176, 156, 157, 177; 219/201, 522; 359/512, 656, 834; 392/408, 409

[56] References Cited

U.S. PATENT DOCUMENTS

| | | | |
|---|---|---|---|
| 281,224 | 7/1883 | Goodsell et al. | 600/169 X |
| 1,934,110 | 11/1933 | Wilson | 600/169 X |
| 4,076,018 | 2/1978 | Heckele | 128/6 |
| 4,279,246 | 7/1981 | Chikama | 128/6 |
| 4,722,000 | 1/1988 | Chatenever | 600/169 X |
| 5,448,990 | 9/1995 | De Faria-Correa | 600/177 X |

FOREIGN PATENT DOCUMENTS

| | | | |
|---|---|---|---|
| 0217316 | 9/1988 | Japan | 128/4 |

Primary Examiner—Richard J. Apley
Assistant Examiner—Beverly M. Flanagan
Attorney, Agent, or Firm—Pandiscio & Pandiscio

[57] ABSTRACT

A fog-free endoscope comprises an elongated tube defining an optical path extending from a distal end of the endoscope. A front window is fixed to the endoscope distal end, and heating means is disposed in the endoscope proximate the window to provide heat to the window to maintain the window in a fog-free condition.

1 Claim, 5 Drawing Sheets

FOG-FREE ENDOSCOPE

FIELD OF THE INVENTION

This invention relates to endoscopes in general and, more particularly, to endoscopes wherein the distal-most optical lens, or window, is kept free of thermally-induced fog.

BACKGROUND OF THE INVENTION

In endoscopic surgical procedures, relatively narrow surgical instruments are inserted into a patient's body so that the distal ends of the instruments are positioned at a remote interior site, while the proximal ends of the instruments remain outside the patient's body. The surgeon manipulates the proximal ends of the instruments as required to cause the distal ends of the instruments to carry out the desired surgical procedure at the remote interior site.

In order to visualize the remote interior site, the surgeon also inserts an endoscope into the body during the endoscopic surgery, together with, or including, an appropriate source of illumination.

The endoscope generally comprises an elongated shaft having a distal end and a proximal end, and an internal passageway extending between the distal and proximal ends. At the distal end is disposed a window and proximate thereto, within the shaft, is disposed an image capturing means, such as an objective lens and, proximally thereof, image conveying means, such as relay lenses. The latter extend through the internal passageway of the shaft. Accordingly, the image capturing means captures an image of a selected region located substantially adjacent the distal end of the shaft, and the image conveying means relays the image provided by the image capturing means to the proximal end of the shaft. Viewing means, such as one or more eye pieces, or electronic display apparatus, disposed adjacent the proximal end of the shaft, present the image obtained by the image capturing means and conveyed by the image conveying means, in such manner as to be viewed by the surgeon.

The image capturing means, conveying means, and viewing means commonly utilize one of several different arrangements to capture an image at the distal end of the shaft and to present it to the surgeon.

For example, in one arrangement, the image capturing means comprise a bundle of fiber optic filaments which extend through the internal passageway of the shaft. A front window and an objective lens are positioned at the distal end of the shaft to focus the desired image onto the distal end of the fiber optic bundle. The fiber optic bundle conveys the captured image to the proximal end of the shaft, where it is received by viewing means. In this arrangement, the viewing means may comprise a conventional optical viewer, or eyepiece, which is viewed directly by the surgeon. Alternatively, the viewing means may comprise an appropriate image sensor, e.g., a charge coupled device (CCD), or video tube, which can receive the captured image from the proximal end of the fiber optic bundle and generate corresponding video signals representative of the captured image. The video signals are then displayed on an appropriate display device (e.g., a monitor) which is viewed by the surgeon.

In a second arrangement, the image capturing means comprise a CCD which is disposed at the distal end of the shaft, and wires for conveying the image extend through the internal passageway of the shaft. An appropriate objective lens, behind a front window, focuses the desired image onto the CCD image-receiving surface, and the wires convey the CCD element video output signals to the proximal end of the shaft. The video signals are then displayed on an appropriate display device which is viewed by the surgeon.

In a third arrangement, the image capturing means comprise a front rod-lens system. In this embodiment, an objective lens, behind a front window, focuses the desired image onto the first of a series of rod-lens elements arranged within the internal passageway of the shaft so as to capture the desired image at the distal end of the shaft and convey that image to viewing means located at the proximal end of the shaft. With this arrangement, the viewing means can comprise a display device in the form of a conventional optical viewer, or eyepiece, which is viewed directly by the surgeon. Alternatively, the viewing means can comprise an appropriate image sensor, e.g., a CCD element or video tube, which can receive the captured image from the proximal end of the rod-lens system and generate corresponding video signals which are representative of the captured image. These video signals are then displayed on an appropriate display device viewed by the surgeon.

Some of the above and other combinations of image capturing, conveying and viewing means are disclosed in U.S. Pat. No. 4,491,865, issued Jan. 1, 1985 to D. Dana et al; U.S. Pat. No. 4,867,137, issued Sep. 19, 1985 to Y. Takahashi; U.S. Pat. No. 4,879,992, issued Nov. 14, 1989 to S. Nishigaki et al; and U.S. Pat. No. 4,364,629, issued Dec. 21, 1982 to W. H. Lang et al.

Regardless of the particular construction involved, all prior art endoscope viewing systems tend to suffer from a significant deficiency. When an endoscope at room temperature is inserted into a patient, the difference in temperature between the room and the patient's body usually is such as to cause fogging of the front window of the endoscope. Regardless of the type of image capturing, conveying and viewing means utilized, a window occluded by fog prevents the presentation of a clear view to the surgeon.

Under current practices, the fogging problem is addressed by pre-heating the window and/or pre-treating the window with an anti-fogging agent. In addition, the endoscope often is removed from the working environment and cleaned with a cloth, or the like. The pre-heating, pre-treating, and cleaning must be carried out with sterile materials, using sterile techniques. Such practices lead to increased costs and generate biohazardous wastes.

Thus, there is a need for an endoscope in which the front window is self-maintained fog-free in the presence of substantial differences between room temperature and patient body temperature.

OBJECT OF THE INVENTION

Accordingly, the object of the present invention is to provide an endoscope having a front window maintained in a fog-free condition during a surgical operation.

SUMMARY OF THE INVENTION

The above and other objects of the present invention are addressed by the provision and use of a novel fog-free endoscope which comprises an elongated tube defining an optical path extending from a distal end of the endoscope toward a proximal end of the endoscope. A front window is fixed to the endoscope distal end, and heating means is disposed in the endoscope proximate the window to provide heat to the window.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

The above and other objects and features of the present invention will be more fully disclosed or rendered obvious by the following detailed description of the preferred embodiments of the invention, which, is to be considered together with the accompanying drawings wherein like numbers refer to like parts, and further wherein.

DETAILED DESCRIPTION OF THE PREFERRED EMBODIMENTS

Figure 1:
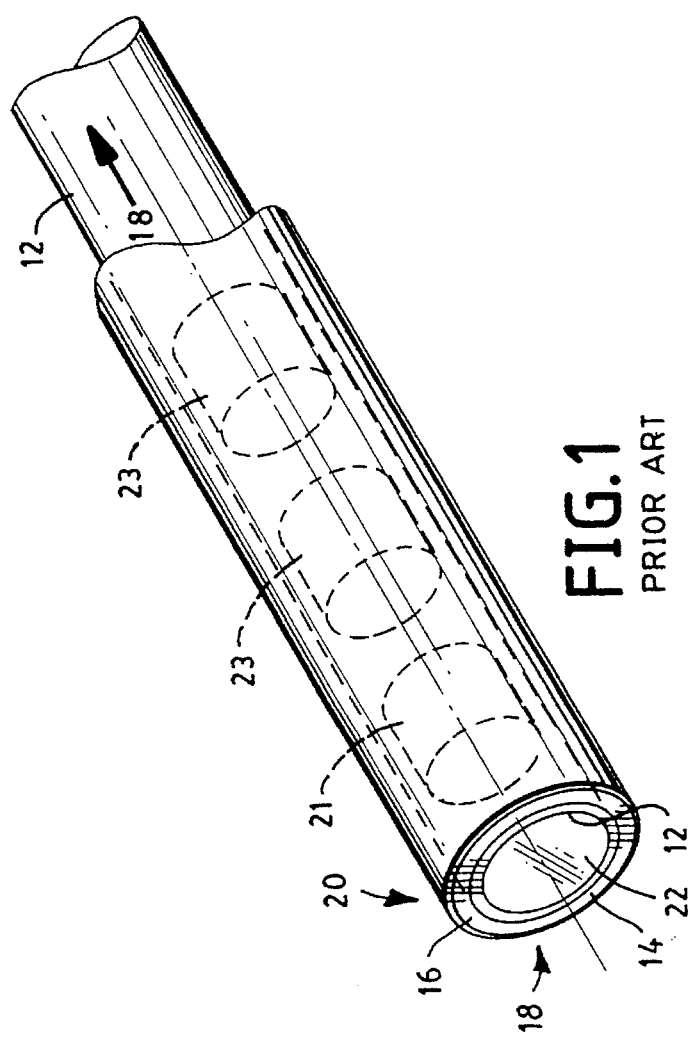
FIG. 1 is a perspective view of a distal end of a prior art endoscope of the type in which the present invention finds utility.
Figure 2:
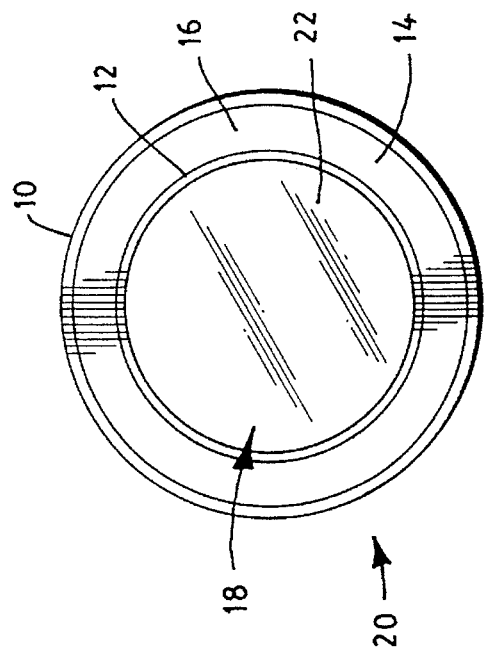
FIG. 2 is a distal end view of the prior art endoscope of FIG. 1.

Referring to FIGS. 1 and 2, there is shown an illustrative example of the type of prior art endoscope in which the present invention finds utility. The prior art endoscope illustrated includes an elongated outer tube 10, typically of a substantially cylindrical configuration. Disposed within the outer tube 10 is an elongated objective tube 12. The outer and objective tubes 10, 12 form therebetween an illumination channel 14, in which are disposed illumination fibers 16, or other light-providing medium.

The objective tube 12 defines an optical path 18 extending from a distal end 20 toward a proximal end (not shown) of the endoscope. A lens, or front window 22, is fixed to the distal end 20 of the endoscope Disposed in the objective tube 12 are objective and relay lenses 21, 23, illustrated in FIG. 1, or other image capturing and relay means (not shown).

Figure 3:
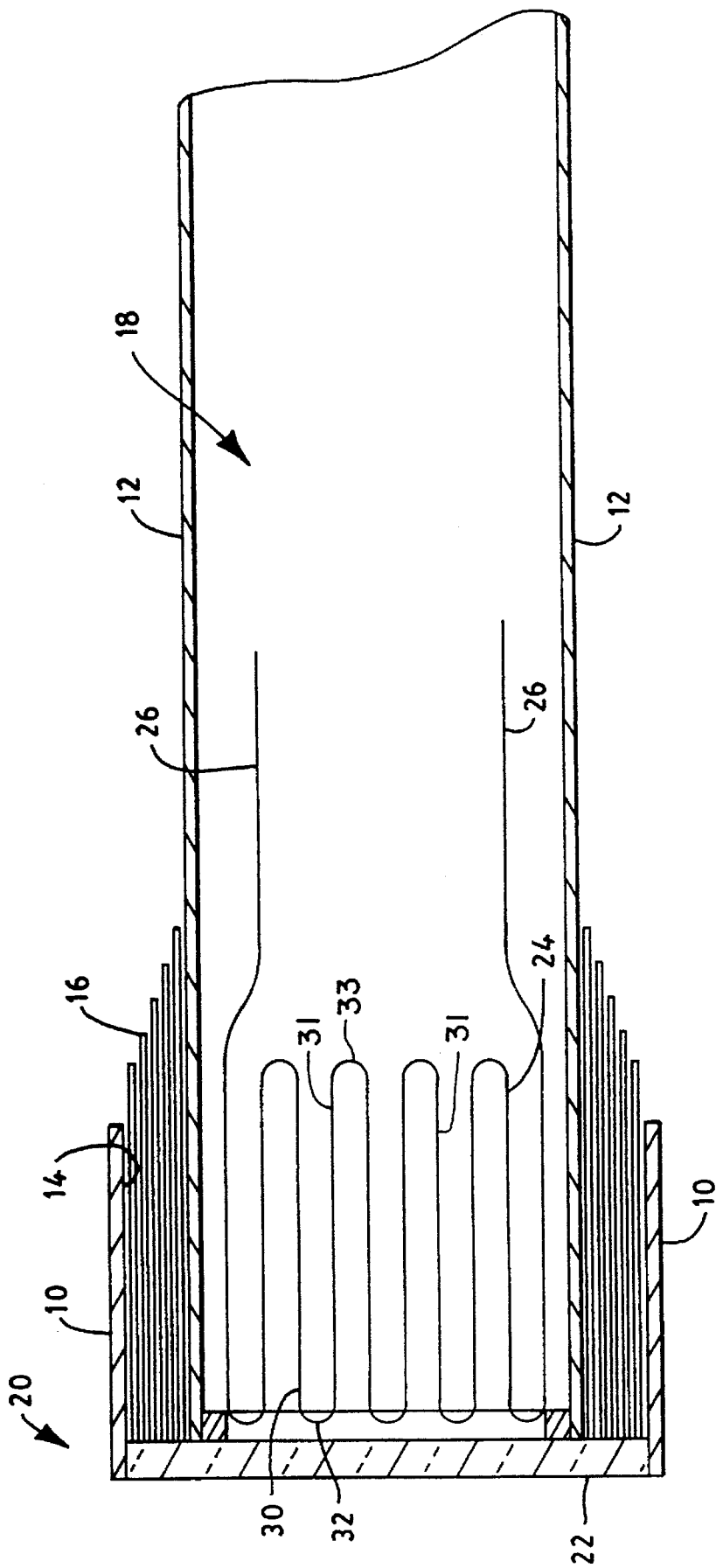
FIG. 3 is a diagrammatic view of one form of fog-free endoscope illustrative of an embodiment of the invention.
Figure 6:
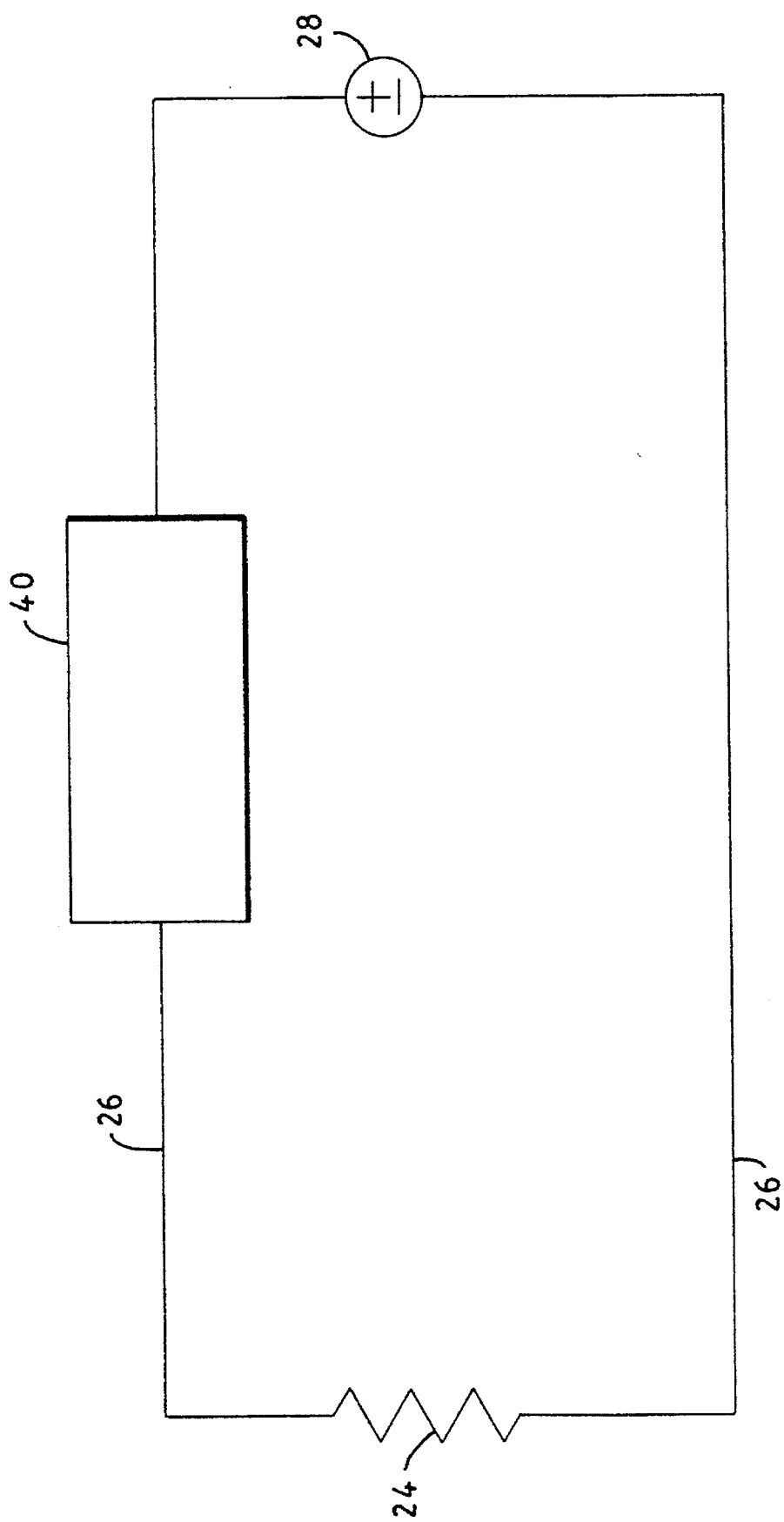
FIG. 6 is a schematic representation of an electrical circuit for the embodiments of the invention shown in FIGS. 3–5.

Referring to FIG. 3, it will be seen that a thermoelectric heating means 24 is disposed in the endoscope proximate the window 22 and extends around the periphery of the window 22. Referring to FIG. 6, electrically conductive wire leads 26 extend through the endoscope proximally to a power source 28. In the embodiment shown in FIG. 3, the thermoelectric heating means 24 comprises a wire coil 30 comprising a series of elongated axially-extending portions 31 defining distal bend portions 32 between neighboring ones of the axially extending portions 31 and disposed adjacent the window 22 and slightly spaced therefrom. The axially-extending portions 31 further define proximal bend portions 33 between neighboring ones of the axially-extending portions 31 and disposed proximally of the window 22 and the distal bend portions 31. In operation, the coil 30 raises the temperature of the entire distal end portion 20 of the endoscope, thereby raising the temperature of the window 22, to maintain the window 22 in a fog-free condition.

Figure 4:
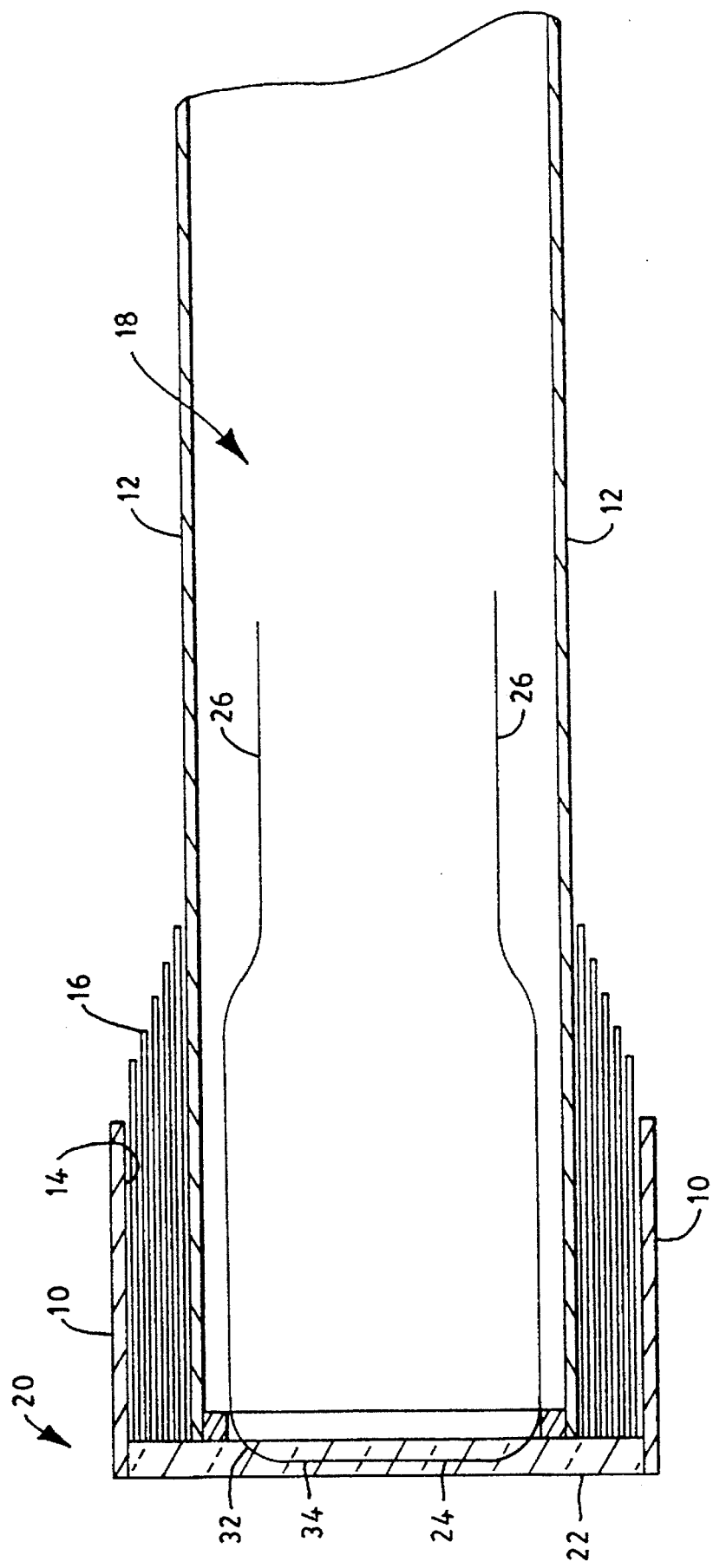
FIG. 4 is similar to FIG. 3, but illustrative of an alternative embodiment of the invention.

Alternatively, the thermoelectric heating means 24 may comprise a coil, or one or more electrically conductive wires 34, fixed to, or embedded in, the window 22 (FIG. 4). In this embodiment, the heating means 24 imparts heat directly to the window 22, to maintain the window free of moisture and fog.

Figure 5:
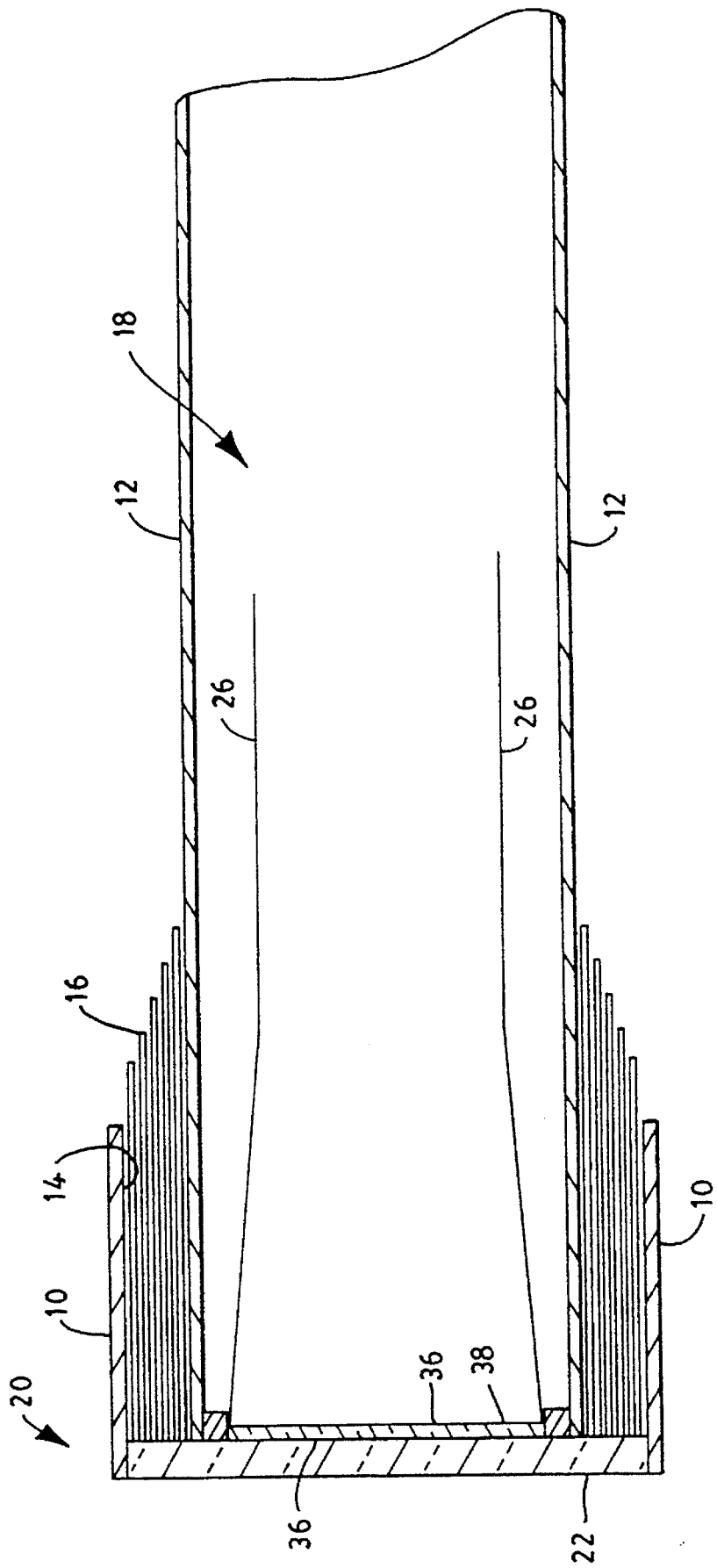
FIG. 5 is similar to FIGS. 3 and 4, but illustrative of a further alternative embodiment of the invention.

Referring to FIG. 5, it will be seen that in another alternative embodiment the thermoelectric heating means 24 comprises an electrically conductive coating 36 applied to an inside surface 38 of the window 22, with the electrically conductive wire leads 26 connected thereto and extending to the power source 28 (as shown in FIG. 6). The coating 36 may comprise a film of optically transmissive, electrically resistive metal, such as that sold under the name of "Iconel 600", or may be a film of optically transmissive electrically resistive plastic, such as that sold under the name of "Mylar".

The power source 28 may comprise a battery or a connection by which an outside power source (not shown) is placed in communication with the heating means 24. The endoscope may also be provided with a control system 40 for selective governance of the temperature of the window 22.

There is thus provided an endoscope having a front window adapted to be maintained in a fog-free condition during a surgical operation.

It is to be understood that the present invention is by no means limited to the particular construction herein disclosed and/or shown in the drawings, but also comprises any modifications or equivalents within the scope of the claims.

What is claimed is:

1. A fog-free endoscope comprising:

an elongated tube having a distal end and defining an optical path extending from said distal end of said endoscope;

a front window fixed to said endoscope distal end; and an electrically conductive wire coil disposed in said distal end of said endoscope, wherein said wire coil is disposed around the periphery of said window, said wire coil comprising a series of elongated axially-extending portions defining distal bend portions between neighboring ones of said axially extending portions and disposed adjacent to and spaced from said window and defining proximal bend portions between neighboring ones of said axially extending portions and disposed proximally of said window and said distal bend portions;

whereby said wire coil is operative to raise the temperature of a distal end portion of said endoscope, thereby to raise the temperature of said window, to maintain said window in a fog-free condition.

* * * * *